US00PP08194P

United States Patent [19]

Brooks, deceased et al.

[11] Patent Number: Plant 8,194

[45] Date of Patent: Apr. 6, 1993

[54] CHERRY ROOTSTOCK: BROOKS-2 CULTIVAR

[76] Inventors: Lyle A. Brooks, deceased, late of Forest Grove, Oreg.; by Wallace E. Heuser, legal representative, P.O. Box 578, Hartford, Mich. 49057

[21] Appl. No.: 825,751

[22] Filed: Jan. 23, 1992

Related U.S. Application Data

[63] Continuation of Ser. No. 371,654, Jun. 19, 1989, abandoned, which is a continuation of Ser. No. 165,221, Mar. 7, 1988, abandoned.

[51] Int. Cl.[5] ..... A01H 5/00

[52] U.S. Cl. ..... Plt./37

[58] Field of Search ..... Plt./37

[56] References Cited

U.S. PATENT DOCUMENTS

| | | | |
|---|---|---|---|
| P.P. 5,159 | 12/1983 | Tydeman, deceased et al. | Plt. 37 |
| P.P. 5,801 | 11/1986 | Monin et al. | Plt. 37 |
| P.P. 5,802 | 11/1986 | Monin et al. | Plt. 37 |
| P.P. 5,803 | 11/1986 | Monin et al. | Plt. 37 |
| P.P. 6,676 | 3/1989 | Hansche | Plt. 37 |

*Primary Examiner*—Howard J. Locker
*Attorney, Agent, or Firm*—Dykema Gossett

[57] ABSTRACT

This is a new and distinct cherry tree, given the varietal name of "Brooks-2 Cultivar," which will be marketed under the name "MXM-2" Cultivar. It is characterized by its strong resistance to Phytophthora species and *Agrobacterium tumifaciens*. It is also adaptable to a wide variety of soil types.

3 Drawing Sheets

This application is a continuation of Ser. No. 07/371,654, filed Jun. 19, 1989 (abandoned), which in turn was a continuation of Ser. No. 07/165,221, filed Mar. 7, 1988 (abandoned).

BACKGROUND OF THE INVENTION

This distinct new cherry cultivar was discovered during the Summer of 1958 by Lyle A. Brooks, who resided at 2515 Gales Way, Forrest Grove, Oreg. 97116. It was selected from a population of approximately 30,000 open pollinated *Prunus mahaleb* seedlings growing in a nursery field near Fairview, Oreg. The seed used to grow these *Prunus mahaleb* seedlings came from a seed orchard that had *Prunus mahaleb* and *Prunus avium* fruiting trees growing side by side. During the Spring of 1957 a rare weather occurrence brought the bloom period of both these species together, resulting in a small portion of the seed population having *Prunus mahaleb* as the seed parent and *Prunus avium* as the pollen parent. During the Summer of 1958, the inventor, Lyle A. Brooks, selected 100 specimens exhibiting visual hybrid characteristics from the large 30,000 seedling population. Brooks then started a screening and evaluation process with the goal of producing an improved cherry rootstock. The rootstock screening process included comparison with various common scion varieties. Investigations were made respecting clonal rooting ability, disease resistance, hardiness and compatibility, precocity, productivity and tree size. The Brooks-2 cultivar was found in a cultivated area near Fairview, Oreg., and was asexually reproduced by Lyle A. Brooks by softwood cuttings near Fairview, Oreg. The asexually reproduced Brooks-2 cultivar firmly retain the unique combination of characteristics as disclosed herein as defining the cultivar for which patent protection is sought.

Brooks-2 cultivar as a rootstock produces a tree that has been compatible with all scion varieties tested to date. The finished tree size, with Brooks-2 as the rootstock, is large, making a tree similar in size to that produced by clonal *Prunus avium* F 12/1 and approximately 20% larger than trees on *Prunus mahaleb* rootstock. The variety has a wide range of soil adaptability from lighter sands to heavy clay types and consistently produces a long-lived, well-anchored tree without root suckers. It is very resistant to *Phytophthora cactorum* and several other Phytophthora species as well as *Agrobacterium tumifaciens.*

The upper surfaces of the leaves of the parent varieties, *Prunus mahaleb* and *Prunus avium*, are substantially different than those of Brooks-2. The leaves of *Prunus mahaleb* are generally light green and those of *Prunus avium* are a dull, dark green.

Brooks-2 as a rootstock results in earlier production of fruit of the grafted plants than with the parent varieties and is healthier than either parent. Brooks-2 has substantially greater longevity than either *Prunus mahaleb* or *Prunus avium* and can survive in a greater range of climates and soil than the parent varieties, particularly in heavier, slow draining soil.

DETAILED DESCRIPTION

Figure 1:
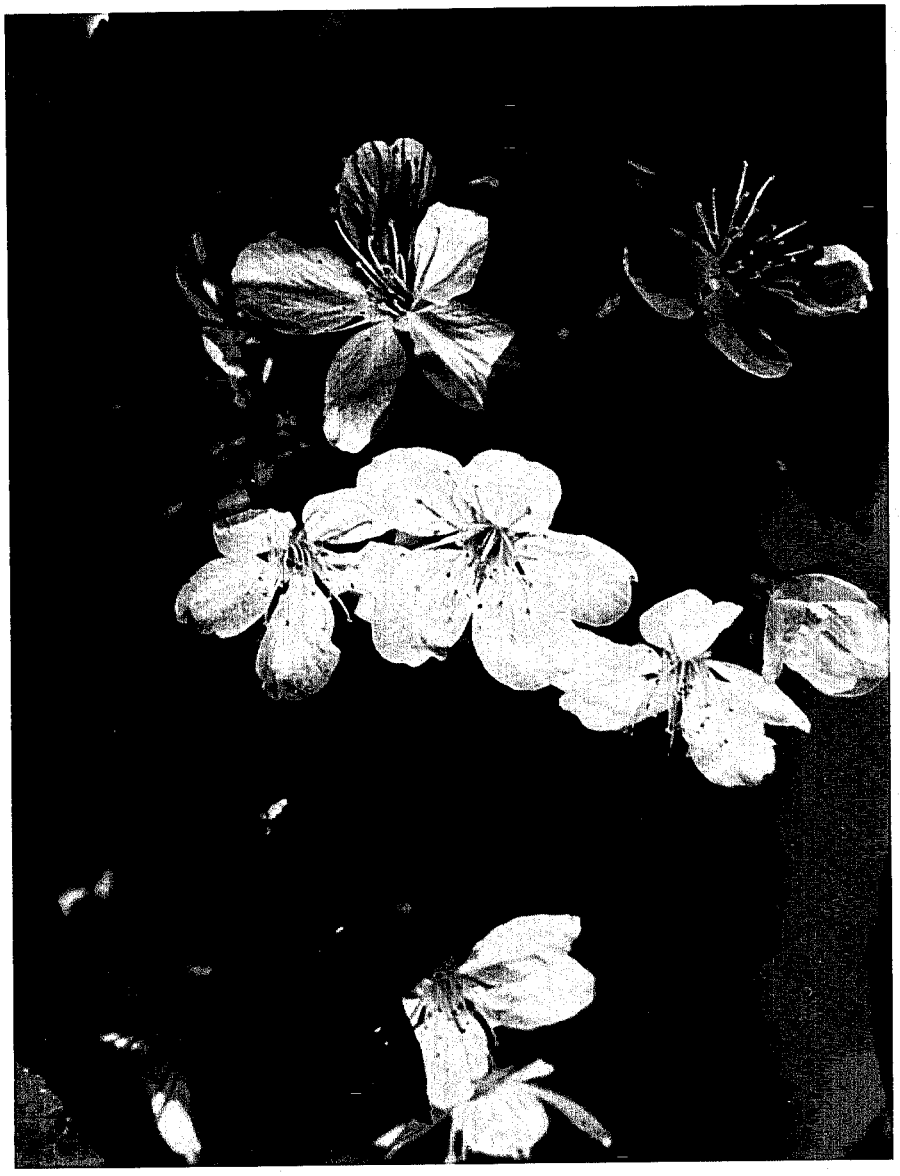
FIG. 1 illustrates a branch, leaves and flower cluster of Brooks-2; the petals are white (RHS plate 155D).
Figure 2:
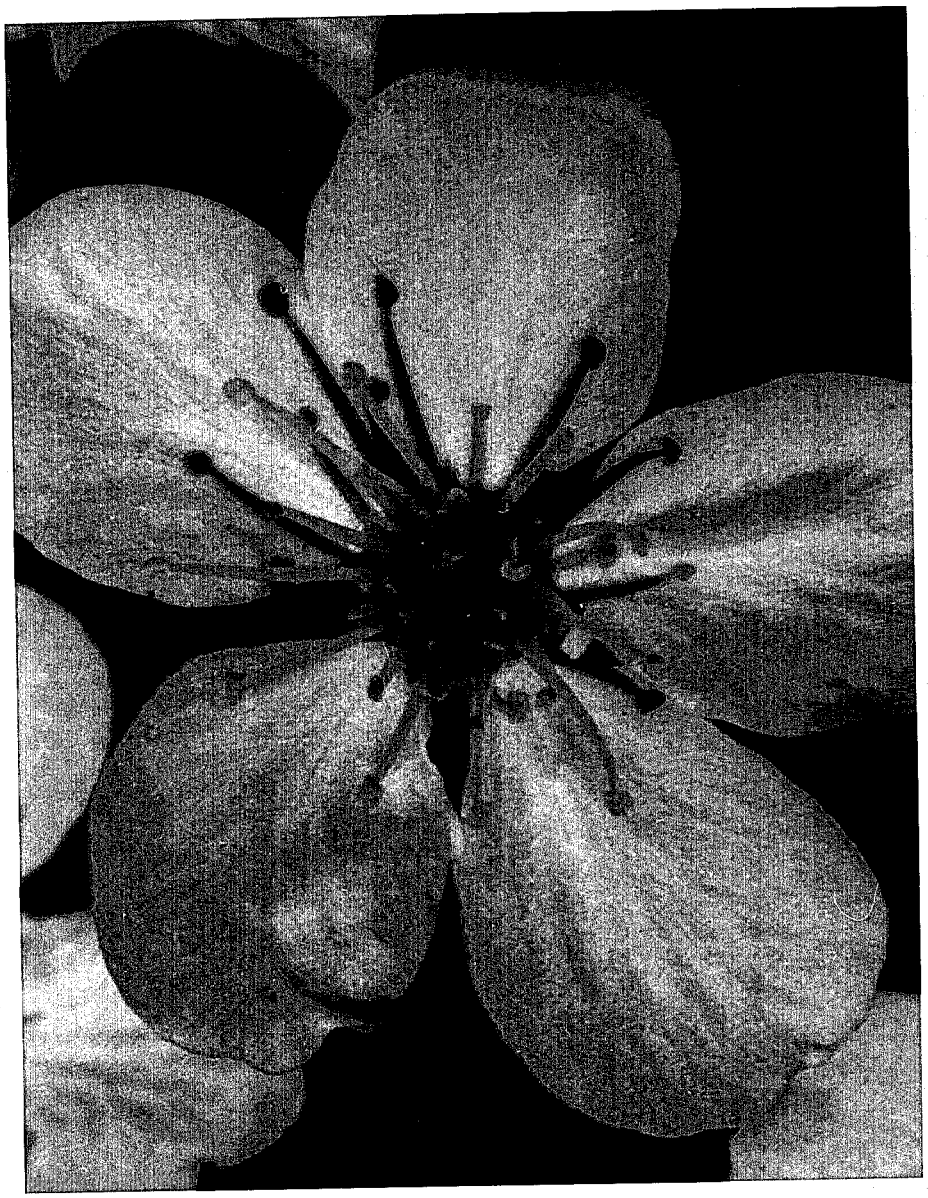
FIG. 2 is a close up of Brooks-2 flowers.
Figure 3:
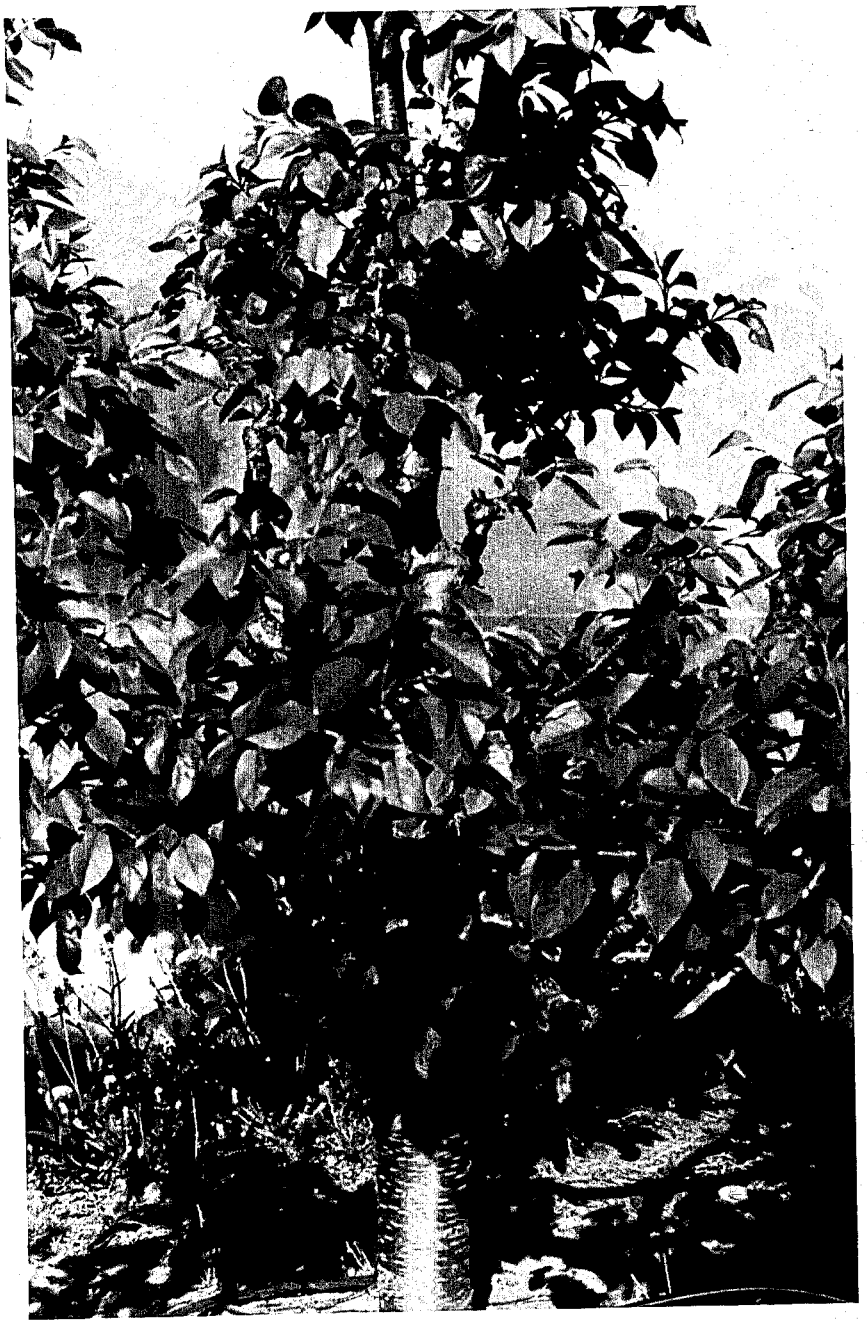
FIG. 3 is a whole-tree view of Brooks-2.

This new cultivar serves as a support for other cherry tree cultivars grafted thereon. To applicant's knowledge, the rootstock per se has not been fruited and thus a description of the fruit is not available. Therefore, the fruit and seed produced on the rootstock depend upon the characteristics of the cherry tree cultivars which are grafted thereon.

Leaves:

*Size.*—Width 4.0 to 4.4 cm; Length 8.0 to 8.5 cm.

*Shape.*—Simply oblate with rounded base and acuminate tip with margins irregularly serrated and some teeth tipped with small, dark glands.

*Surface.*—Upper surface glabrous, lower surface with fine, white leaf hairs along midriff and primary veins; pronounced veins.

*Color.*—Non-glossy olive green (RHS plate 137A on upper surface, light green (RHS plate 147B) on lower surface.

Petiole:

*Color.*—Red-Purple (RHS plate 59A).

*Pubescence.*—Very fine, short, white, scattered hairs.

*Margin.*—Smooth.

*Shape.*—Narrow, slender, light green, with light reddish color developing at base of petiole.

*Glands.*—2 prominent uniform glands at base of leaf blade.

*Stipules.*—None.

*Length.*—1.8 to 2.0 cm.

Flower:

*Description.*—White, simple, 5 petals, 25 anthers, 1 pistil.

*Petals.*—Round, 7 mm, slightly pointed where attached.

*Stem.*—1.7 to 2 cm average length.

*Blossoms.*—5–6 blossoms per flower bud.

Buds:

*Length.*—0.3 to 0.4 cm., tight, medium brown, conical, 3/1 Phyllotaxy. (3 nodes/Revolution).

Root system: Very fibrous, more so than either parent variety.

General growth habit: Vigorous, spreading, good caliper in wood; slightly branched in nursery row. A ten year study has demonstrated that Brooks-2 has greater longevity than either parent variety. The trunk of a four year tree is on average approximately 62 $cm^2$ in cross-section.

Wood:

*Color.*—Light, greyish to light brown.

*Texture.*—Smooth, strong.

*Internodes.*—2.0 to 2.5 cm on current seasons growth.

*Lenticels.*—Few, scattered but more conspicuous in summer, slightly lenticular, raised, light brown.

*Tree size.*—(Of scion) Large, equal to *Prunus avium* F 12/1.

Fruit: The fruit of Brooks-2 has not been observed. It is believed that Brooks-2 is sterile.

It is claimed:

1. A cherry tree rootstock plant substantially as herein described and illustrated.

* * * * *